United States Patent

Dillon et al.

[11] Patent Number: 5,827,239
[45] Date of Patent: Oct. 27, 1998

[54] PROTECTION ASSEMBLY

[75] Inventors: Jagmohanbir Singh Dillon, Bonython; William Leonard Mobbs, Wanniassa, both of Australia

[73] Assignee: Noble House Group Pty. Ltd., Wanniassa, Australia

[21] Appl. No.: 714,119
[22] PCT Filed: Mar. 9, 1995
[86] PCT No.: PCT/AU95/00119
§ 371 Date: Sep. 9, 1996
§ 102(e) Date: Sep. 9, 1996
[87] PCT Pub. No.: WO95/24332
PCT Pub. Date: Sep. 14, 1995

[30] Foreign Application Priority Data

Mar. 9, 1994 [AU] Australia ............................ PM4327

[51] Int. Cl.⁶ ............................................ A61M 5/00
[52] U.S. Cl. ............................................ 604/263; 604/177
[58] Field of Search ................................ 604/177, 263

[56] References Cited

U.S. PATENT DOCUMENTS

| 5,112,311 | 5/1992 | Utterberg et al. .............. 604/177 |
|---|---|---|
| 5,120,320 | 6/1992 | Faynfold ........................ 604/177 |
| 5,350,368 | 9/1994 | Sheilds ......................... 604/263 |

FOREIGN PATENT DOCUMENTS

| 0 425 448 | 5/1991 | European Pat. Off. ......... A61M 5/32 |
|---|---|---|
| 0 475 857 | 3/1992 | European Pat. Off. ......... A61M 5/32 |
| 2 263 789 | of 0000 | France ........................ A61M 25/00 |
| WO 90/03196 | 4/1990 | WIPO ........................... A61M 5/32 |
| WO 92/11885 | 7/1992 | WIPO ........................... A61M 5/32 |

Primary Examiner—Gary Jackson
Attorney, Agent, or Firm—Michael D. Bednarek; Kilpatrick Stockton LLP

[57] ABSTRACT

A protection assembly (22) for a wing catheter (10) is described, the protection assembly having: a sleeve member (24) adapted to be longitudinally displaced relative to the wing catheter from a needle exposed position to a needle protected position; and fixing means for fixing the sleeve member in the needle protected position, wherein the sleeve member comprises a pair of submembers (26, 28) adapted to be locked together to form the sleeve member, the submembers defining open-ended slots therebetween for receiving the wing (18, 20) of the wing catheter.

9 Claims, 2 Drawing Sheets

PROTECTION ASSEMBLY

TECHNICAL FIELD

Due to the existence of transmissable diseases such as HIV and Hepatitis, there are concerns regarding the potential of needle-stick injury to medical staff when handling wing catheters.

This invention relates to a protection assembly for protecting against needle-stick injury by a wing catheter.

As used herein, the term "catheter" is used to denote medical and veterinary devices for the purpose of infusing liquids or medication or, alternatively, for drawing off liquid such as, for example, occurs during the donation of blood. Accordingly, the term "catheter" includes within its scope wing needles, cannulas and other like devices for the intravenous, intramuscular or hypodermic injection of a substance into a human or other animal body, or for the removal of a substance (eg. blood) from a human or other animal body.

As used herein the term "wing" is used to denote a protrusion which extends transversely relative to the longitudinal extent of the catheter. Typically, there are a pair of protrusions extending in generally opposite transverse directions from the catheter. Such arrangements are sometimes referred to as "butterfly wings".

BACKGROUND ART

A number of protection assemblies for wing catheters have been proposed. They range from simple slotted cylinders to complex protection assemblies.

Known is a protection assembly for a wing catheter as taught in U.S. Pat. No. 5,112,311 in the name of Utterberg. In the arrangement illustrated in FIG. 15 of this patent, longitudinally extending slots are cut or formed in each of a pair of articulated sub-members in the form of semi-cylindrical shells. The protection assembly must be assembled on the catheter during manufacture, or at least prior to use, with the wings of the catheter being carefully extended through the respective slots as the semi-cylindrical shells are folded together.

Also known is a protection assembly according to the teaching of Australian Patent 650317 in the name of Becton. In this arrangement, a pair of sub-members of the protection assembly are folded or fixed together to create a pair of longitudinally extending closed slots. As with the teaching of Utterberg, the protection assembly must be located on the wing catheter during manufacture, or at least prior to use of the wing catheter.

DISCLOSURE OF THE INVENTION

This invention in one aspect resides broadly in a protection assembly for a wing catheter, the protection assembly including:

a sleeve member adapted to be longitudinally displaced relative to the wing catheter from a needle exposed position to a needle protected position; and fixing means for fixing the sleeve member in the needle protected position, wherein the sleeve member comprises a pair of sub-members adapted to be locked together to form the sleeve member, the sub-members defining open-ended slots therebetween for receiving the wing of the wing catheter.

The sub-members may be separate and adapted to fit together by clip-locking or snap-acting fasteners. However it is preferred that the sub-members are articulated by hinge means extending along a portion of a common longitudinal edge. The hinge means can be affixed to each sub-member. Alternatively and preferably, the hinge means is integral with the sub-members.

Preferably also, the fixing means is a profile in at least one longitudinal edge of at least one sub-member, the profile adapted to retain the wing of the wing catheter in the needle protected position. In a preferred embodiment both longitudinal edges of both sub-members are profiled. Alternatively, the fixing means may include deformable plugs, ramps or engagement means peripherally disposed about the interior of the sleeve member and adapted to be non-releasably engaged by corresponding means associated with the needle. The fixing means may include a plurality of resilient spines adapted to engage with corresponding spines associated with the needle to allow movement of the sleeve member to a position enclosing the point of the needle but to prevent movement of the sleeve member away from this position.

In a preferred embodiment, the sub-members include primary locking means opposite the hinge means. The sub-members may include secondary locking means at a position longitudinally spaced from the primary locking means to resist transverse spreading of the sub-members and resultant widening of the open-ended slots. In a preferred embodiment the locking means are located proximate opposed longitudinal edges of the sub-members. The locking means can include a variety of suitable forms. For example, the locking means can be a contact adhesive. In a preferred embodiment the locking means includes deformable plug means proximate one of the opposed longitudinal edges and receiving means proximate the other edge for non-releasably receiving the deformable plug means. Alternatively again, the locking means can be a circlip adapted to snap about a portion of the periphery of the sleeve member. In another preferred embodiment the locking means is constituted by a snap action hinge operable between an open position in which the articulated sub-members are positioned apart for pivotal movement relative to one another and a closed position in which the sub-members are positioned together and pivotal movement relative to one another is prevented.

Advantageously, the sleeve member can be assembled on the tube of the wing catheter whilst the catheter is in use.

The sub-members can take a variety of shapes and forms. They could for example be substantially planar and hinged together to form a square, rectangular, hexagonal or other shaped tubing and in such an arrangement are adapted to conform with a needle mounting or support assembly which is correspondingly shaped. However, it is preferred that the sub-members are substantially semi-cylindrical shells and are articulated to each other by hinge means having an axis substantially parallel to the longitudinal axis of the sleeve member.

In a preferred embodiment, one sub-member includes a generally planar surface for abutting the patient in use, and the other sub-member includes a scalloped surface for facilitating manual displacement of the protection assembly relative to the wing catheter from the needle exposed position to the needle protected position. Preferably, the scalloped surface is adapted to receive transversely extending adhesive tape in use adhered to the patient and locating the protection assembly relative to the patient. With this arrangement the patient can conveniently displace the wing catheter to the needle protected position with a single hand, thereby leaving the other hand free to apply pressure to the puncture wound. For example, in a situation where the catheter is inserted in the patient's left arm, the patient can grasp the tubing with the left hand and can pull whilst the protection assembly is fixed relative to the patient by virtue of the adhesive tape. Hence the catheter is withdrawn and immediately protected by the protection assembly and the right hand is free to apply pressure to the puncture wound.

In another aspect this invention resides broadly in a wing catheter assembly including a protection assembly as defined in any one of the above statements.

In a further aspect this invention resides broadly in a blood collection bag or an intravenous infusion set including a wing catheter assembly as defined above.

In yet another aspect this invention resides broadly in a method of protection against needle stick injury by a wing catheter, the method including:

locking the sub-members of a protection assembly as defined above together about the tube of a wing catheter to constitute the sleeve member;

sliding the protection assembly forward relative to the wing catheter such that the wings of the wing catheter enter the open-ended slots of the protection assembly; and sliding the protection assembly further forward and fixing the sleeve member relative to the wing catheter.

BRIEF DESCRIPTION OF THE FIGURES

In order that this invention may be more easily understood and put into practical effect, reference will now be made to the accompanying drawings which illustrate a preferred embodiment of the invention, wherein.

BEST MODE

Figure 1:
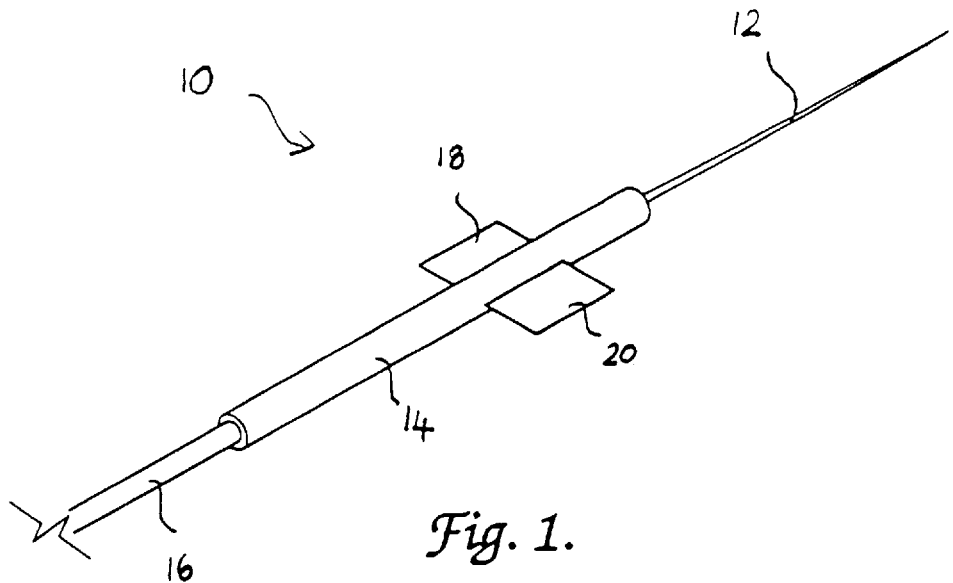
FIG. 1 is an illustration of a conventional wing catheter.

As can be seen in FIG. 1, wing catheter 10 has a needle 12, a needle support 14, and a plastic tube 16 for the infusion or withdrawal of substances through the needle.

A pair of butterfly wings 18 and 20 are provided on needle support 14 for abutment against the skin of a patient when wing catheter 10 is in use. Adhesive tape may be positioned across the wings 18 and 20 and adhered to the skin of the patient to hold wing catheter 10 steady.

Figure 2:
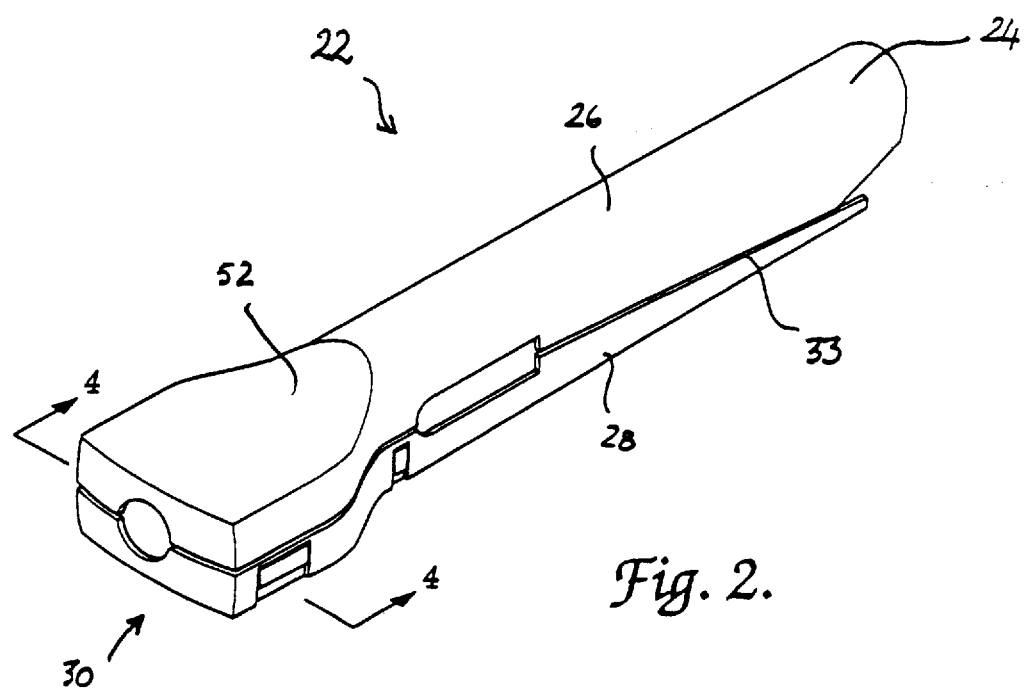
FIG. 2 is a perspective view of a protection assembly in accordance with the invention.
Figure 3:
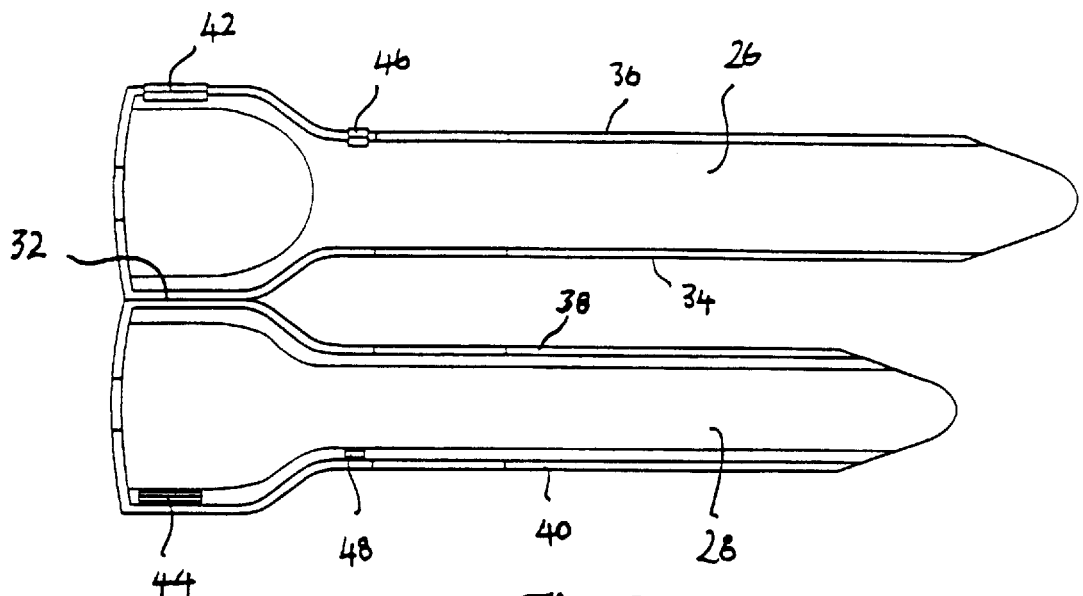
FIG. 3 is a plan view of the protection assembly of FIG. 2 in open configuration.

A protection assembly 22 in accordance with the present invention is illustrated in FIG. 2.

Protection assembly 22 includes a generally cylindrical sleeve member 24. Sleeve member 24 has upper and lower generally semi-cylindrical shell-like sub-members 26 and 28 joined together at annular support end 30 by a longitudinally extending integral hinge means 32. Longitudinally extending open-ended slots 33 are adapted to receive wings 18, 20 of the wing catheter.

Upper sub-member 26 has a pair of opposed longitudinally extending edges 34 and 36, and lower sub-member 28 has a pair of opposed longitudinally extending edges 38 and 40. Longitudinally extending open-ended slots 33 are defined between longitudinally extending edges 34, 38, and 36, 40, respectively, when in the closed configuration.

Edges 34 and 38 meet to form hinge means 32 at annular support end 30. Opposed edges 36 and 40 are adapted to be locked together by primary locking means in the form of tab 42 and tab receiver 44. The opposed edges 36 and 40 are also adapted to be locked together by secondary locking means in the form of tab 46 and tab receiver 48. The secondary locking means prevent excessive transverse spreading of the sub-members and resultant widening of slots 33 defined between the sub-members.

The opposed sub-members 26 and 28 are of unequal length to facilitate the inclination of the catheter and protection assembly when a needle is being removed from a patient.

Figure 4:
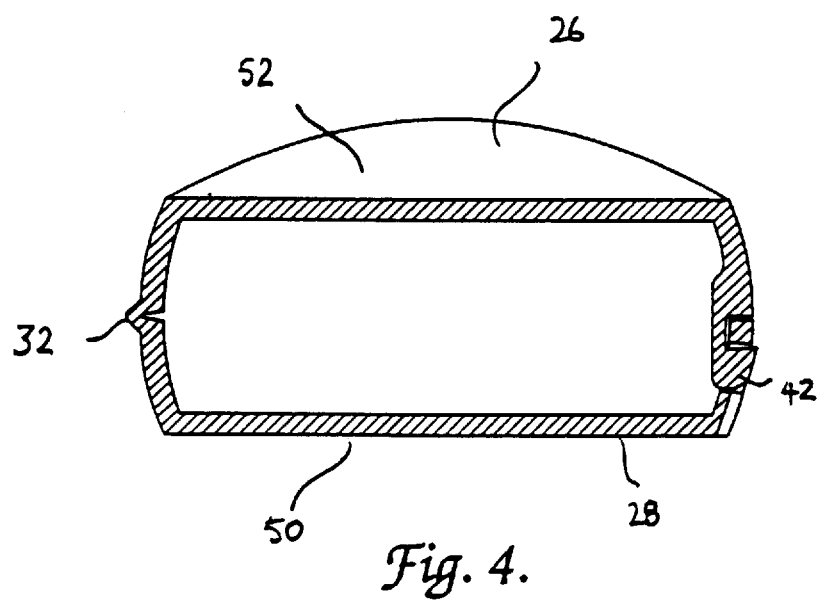
FIG. 4 is a sectional elevation through the annular support end of the protection assembly of FIG. 2 in closed configuration.

As can be seen in FIG. 4, annular support end 30 has two halves which are hinged by integral hinge 32. The halves may be closed by locking together edges 36 and 40 to form the generally cylindrical sleeve member illustrated in FIG. 2.

Tab 42 is resilient and has a chamfered or barbed end which is received within a matching tab receiver 44 and retained therein so as not to permit retraction. The secondary locking means are of similar construction.

Lower sub-member 28 includes a generally planar surface 50 for abutting the patient in use, and upper sub-member 26 includes a scalloped surface 52 for facilitating manual displacement of protection assembly 22 relative to wing catheter 10 from the needle exposed position to the needle protected position. Scalloped surface 52 is adapted to receive transversely extending adhesive tape in use adhered to the patient and locating protection assembly 22 relative to the patient. Scalloped surface 52 is shaped to facilitate manual displacement of the protection assembly with a thumb or the like.

The protector can be made from a range of suitable materials which are preferably durable and resilient. Plastics is a suitable material, but the protector can also be made from a suitable metal.

In use, the protection assembly in accordance with the invention is placed over the plastic tubing of the wing catheter. This can be done when the wing catheter is about to be used or conveniently when the wing catheter is about to be removed from a patient. The two sub-members are squeezed together to lock them together. If desired protection assembly 22 can be fixed relative to the patient with adhesive tape. In that case, protection assembly 22 is fixed whilst wing catheter 10 is withdrawn from the patient into protection assembly 22. Alternatively, protection assembly 22 is pushed forward over the needle point of the wing catheter as it is withdrawn from the patient. This results in the sleeve member locking over the needle point thereby providing protection against needle stick injury. Alternatively, the wing catheter may have been provided with a protection assembly in accordance with the invention during manufacture, the protection assembly having been placed about the plastic tubing and the sub-members locked together during manufacture of the wing catheter.

It will be realised that the protection assembly in accordance with the invention has a number advantages. It provides useful alternatives in manufacturing processes such that the sleeve member can be located on the wing catheter after manufacture of the wing catheter. Conveniently, the protection assembly can be assembled on the tubing immediately prior to withdrawal of the wing catheter from the patient. The protection assembly can be single handedly deployed thereby freeing the other hand of the patient to apply pressure to the puncture wound. The protection assembly affords protection against needle stick injury from wing catheters such as are employed with blood collection bags and intravenous infusion sets. Protection against needle stick injury is afforded not only to users and patients, but also to waste disposal operators.

It will of course be realised that whilst the above has been given by way of an illustrative example of this invention, all such and other modifications and variations hereto, as would be apparent to persons skilled in the art, are deemed to fall within the broad scope and ambit of this invention as is hereinafter claimed.

The claims defining the invention are as follows:

1. A protection assembly for a wing catheter having a plurality of wings, the protection assembly comprising:

a sleeve member adapted to be longitudinally displaced relative to the wing catheter from a needle exposed position to a needle protected position, wherein the sleeve member comprises a pair of submembers adapted to be locked together to form the sleeve member, the sleeve member further comprising open-ended wing receiving means for receiving the wings of the wing catheter, the open-ended wing receiving means being defined between the locked together sub-members, and the sleeve member further comprising fixing means for engaging the winged catheter so as to fix the wing catheter in the needle protected position.

2. A protection assembly as defined in claim 1, wherein the sub-members are articulated by hinge means extending along a portion of a common longitudinal edge.

3. A protection assembly as defined in claim 1 or 2, wherein the fixing means is a profile in at least one longitudinal edge of at least one sub-member, the profile adapted to retain the wing of the wing catheter in the needle protected position.

4. A protection assembly as defined in claim 2, wherein the sub-members include primary locking means opposite the hinge means.

5. A protection assembly as defined in claim 4, wherein the sub-members include secondary locking means at a position longitudinally spaced from the primary locking means to resist transverse spreading of the sub-members and resultant widening of the open-ended slots.

6. A protection assembly as defined in claim 1 or 2, wherein the sleeve member can be assembled on the tube of the wing catheter.

7. A protection assembly as defined in claim 1, wherein one sub-member includes a generally planar surface for abutting the patient in use, and the other sub-member includes a scalloped surface for facilitating manual displacement of the protection assembly relative to the wing catheter from the needle exposed position to the needle protected position.

8. A protection assembly as defined in claim 7, wherein the scalloped surface is adapted to receive transversely extending adhesive tape in use adhered to the patient and locating the protection assembly relative to the patient.

9. A method of protection against needle stick injury by wing catheter, comprising the steps of:

locking the sub-members of a protection assembly together about the tube of a wing catheter to constitute the sleeve member, the protection assembly including:

a sleeve member adapted to be longitudinally displaced relative to the wing catheter from a needle exposed position to a needle protected position, wherein the sleeve member comprises a pair of submembers adapted to be locked together to form the sleeve member, open-ended wing receiving means for receiving the wings of the wing catheter, the open-ended wing receiving means being defined between the locked together sub-members, and fixing means for fixing the sleeve member in the needle protected position, wherein the fixing means includes the open-ended wing receiving means:

sliding the protection assembly forward relative to the wing catheter such that the wings of the wing catheter enter the open-ended wing receiving means of the protection assembly; and sliding the protection assembly further forward and fixing the sleeve member relative to the wing catheter.

* * * * *